United States Patent [19]

Cartwright

[11] Patent Number: 4,589,914
[45] Date of Patent: May 20, 1986

[54] HERBICIDAL COMPOUNDS
[75] Inventor: David Cartwright, Reading, England
[73] Assignee: Imperial Chemical Industries PLC, London, England
[21] Appl. No.: 594,012
[22] Filed: Mar. 27, 1984
[30] Foreign Application Priority Data
  Apr. 8, 1983 [GB] United Kingdom ............ 8309648
[51] Int. Cl.$^4$ .................... A01N 41/06; C07C 143/74
[52] U.S. Cl. ............................ 71/103; 558/423; 560/13; 562/430; 564/79; 564/95
[58] Field of Search .......... 71/103; 260/465 D; 564/79, 84, 97, 99, 95; 560/13; 562/430

[56] References Cited
U.S. PATENT DOCUMENTS
4,285,723 8/1981 Cartwright et al. ............ 71/103

Primary Examiner—Dolph H. Torrence
Attorney, Agent, or Firm—Cushman, Darby & Cushman

[57] ABSTRACT

Herbicidally effective diphenyl ether compounds of the formula:

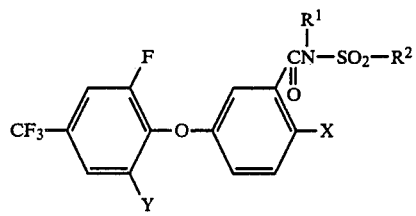

where, for example, X is a halogen atom or a nitro group, $R^1$ is a hydrogen atom or a chlorine, bromine or iodine atom, and $R^2$ is a group $-OR^3$ wherein $R^3$ is an alkyl group containing from 1 to 12 carbon atoms.

6 Claims, No Drawings

HERBICIDAL COMPOUNDS

This invention relates to diphenyl ether compounds, processes for preparing them, and herbicidal compositions and processes utilising them.

According to the present invention there are provided diphenyl ether compounds of the formula (I):

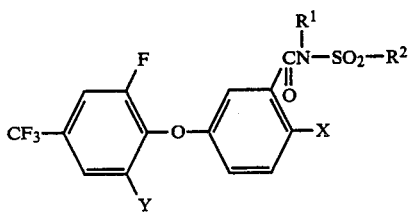

wherein
X is a hydrogen or halogen atom, or an alkyl group (eg. alkyl of 1 to 4 carbon atoms for example methyl) or a nitro or $CF_3$ group;
Y is fluorine or chlorine;
$R^1$ is a hydrogen atom, a source of a hydrogen atom, an alkyl group of 1 to 4 carbon atoms, or an agriculturally acceptable cation; and
$R^2$ is:
(a) a group —OM, wherein M is hydrogen or an agriculturally acceptable cation;
(b) a group —$ZR^3$ wherein Z is oxygen or sulphur and $R^3$ is an optionally substituted aliphatic or alicyclic group of 1 to 12 carbon atoms (preferably 1 to 4 carbon atoms), an optionally substituted phenyl group, or an optionally substituted heterocyclic radical having from 5 to 7 ring atoms;
(c) a group

wherein M is as hereinbefore defined and $R^4$ is defined as for $R^3$ or;
(d) a group —$NR^5R^6$ wherein $R^5$ and $R^6$ are each defined as for $R^3$, and may in addition each represent hydrogen, or one of $R^5$ and $R^6$ may be an alkoxy group of 1 to 4 carbon atoms; furthermore, $R^5$ and $R^6$ together with the nitrogen atom to which they are attached, may form an optionally substituted pyrrolidine, piperidine, or morpholine ring. $R^1$ may inter alia be a hydrogen atom or a source of a hydrogen atom. By the term "a source of a hydrogen atom" we mean an atom or group which is removed during herbicidal use (for example on exposure to moisture) to form a hydrogen atom. As example of such sources of a hydrogen atom there may be mentioned a chlorine, bromine or iodine atom.

Examples of agriculturally acceptable cations include alkali metal and alkaline earth metal cations, for example sodium, potassium, lithium, calcium, and magnesium cations. Further examples include ammonium and substituted ammonium cations, for example such cations containing one, two, three or four alkyl substituents each having from one to six carbon atoms and being optionally substituted for example with hydroxy or phenyl substituents.

Examples of substituents which may be present in $R^3$ when it is an aliphatic or alicyclic group include halogen (ie. chlorine, fluorine, bromine, or iodine), hydroxy, alkoxy (eg. $C_{1-4}$ alkoxy), alkylthio (eg. 1 to 4 carbon atoms), carboxy, alkoxycarbonyl (eg. of 2 to 5 carbon atoms), cyano, or optionally substituted phenyl. When $R^3$ is a phenyl or heterocyclic radical, examples of substituents which may be present include those recited above for the case when $R^3$ is an aliphatic or alicyclic group, and further include alkyl, for example alkyl of 1 to 4 carbon atoms (eg. methyl).

Particular examples of compounds falling within the scope of the invention include the compounds listed in Table 1 below:

TABLE 1

| Compound No. | X | Y | $R^1$ | $R^2$ |
|---|---|---|---|---|
| 1 | $NO_2$ | Cl | H | $OC_2H_5$ |
| 2 | $NO_2$ | Cl | H | —$NHCH_3$ |
| 3 | Cl | Cl | H | —$OCH_3$ |
| 4 | Cl | Cl | H | —$N(CH_3)_2$ |
| 5 | $NO_2$ | Cl | H | —$N(CH_3)_2$ |
| 6 | $NO_2$ | Cl | H | $NH_2$ |
| 7 | $NO_2$ | F | H | —$OC_2H_5$ |
| 8 | $NO_2$ | F | H | —$N(CH_3)_2$ |
| 9 | $NO_2$ | Cl | H | —$NHC_6H_5$ |
| 10 | $NO_2$ | Cl | H | —$NH.C_6H_4.Cl(p)$ |
| 11 | $NO_2$ | Cl | H | $OCH_3$ <br> \| <br> —N—$CH_3$ |

The compounds of the invention may be prepared by a variety of methods. One such method is outlined in Scheme A below:

Scheme A

(II)

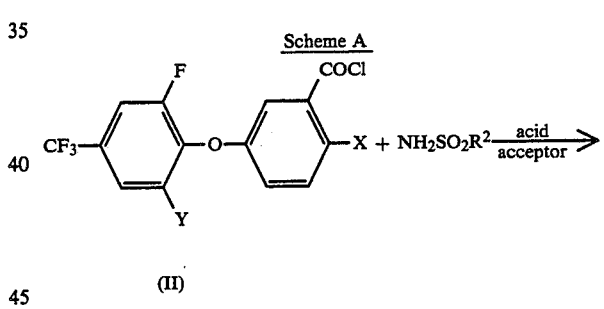

(III)

According to Scheme A, the acid chloride (II) is reacted with the appropriate sulphamate derivative $NH_2SO_2R^2$ in presence of an acid acceptor to give the compound of the invention (III). This may be converted to other compounds of the invention by chemical procedures known in themselves; for example, compounds in which $R^1$ is a cation may be prepared by reacting a compound of formula (III) with the stoichiometric amount, of an alkali metal or alkaline earth metal hydroxide or carbonate, or of ammonia or an amine.

An alternative process for preparing compounds according to the invention is outlined in Scheme B.

Scheme B

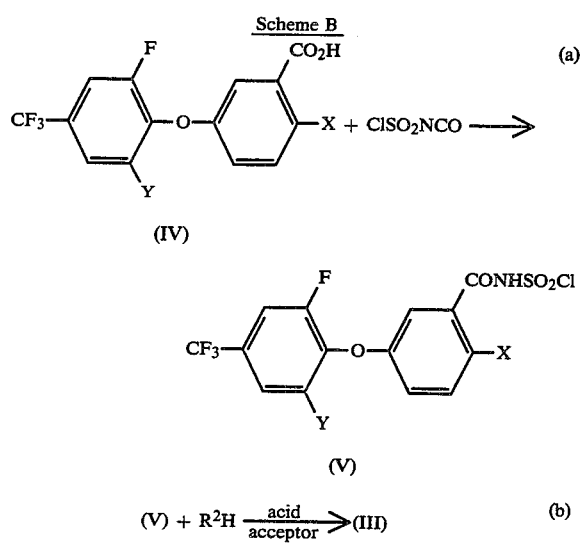

According to step (a) of Scheme B, an acid of formula (IV) is reacted with chlorosulphonyl isocyanate to give the sulphamoyl chloride (V). The reaction is preferably carried out in a solvent or diluent inert towards the reactants. The reaction temperature is preferably from 20° to 100° C., and more preferably from 40° to 80° C. The solvent or diluent may be, for example, a liquid hydrocarbon (eg. toluene) or acetonitrile, or an ether.

In step (b) of Scheme B, the reaction is preferably carried out in a solvent at a temperature from −40° C. to +60° C. and more preferably from −20° C. to +30° C. The acid acceptor may be for example a tertiary amine, for example triethylamine, dimethylaniline, or pyridine. Where the compound $R^2H$ is itself an amine, an excess of the compound $R^2H$ may be used as the acid acceptor.

The starting materials for Schemes A and B above are either known or may be readily prepared by application or adaptation of known methods.

The compounds of the invention are useful as herbicides. In another aspect, therefore, the invention provides a process of inhibiting the growth of unwanted plants, which comprises applying to the plants, or to the locus thereof, a phytotoxic amount of a compound of the formula (I) as hereinbefore defined. The amount of the compound to be applied in the process may vary, depending upon the particular compound chosen, and the identity of the plant species whose growth is to be inhibited, but in general amounts from 0.1 to 10 kilograms per hectare will be suitable; in many cases from 0.25 to 1.0 kilograms per hectare will be appropriate. The skilled worker in the herbicide art will readily be able to establish appropriate application rates by standard procedures without undue experimentation.

The compounds of the invention are effective in controlling a variety of unwanted plants. The compounds may be applied to the above-ground parts of unwanted plants (post-emergence application) or they may be applied to the soil to prevent the growth of plants from seeds present in the soil (pre-emergence application). The compounds may be used, for example, for selective control of weeds in soya bean crops.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecyl-benzenesulphonate, sodium, calcium and ammonium lignosulphonate, butylnaphthalene sulphonate, and a mixture of the sodium salts of diisopropyl- and triisopropyl-naph-thalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example, oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents.

The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention can be used in association (for example in the form of a mixture) with another herbicide.

Examples of such herbicides are:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichloroprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (b 2,4-DB), 2-(4-chloro-2-methylphenoxy)propionic acid (mecoprop), and their derivatives (eg. salts, esters and amides);

C. 3-[4-(4-halophenoxy)phenyl]-1,1-dialkylureas such as 3-[4-(4-chlorophenoxy)phenyl]-1,1-dimethylurea (chloroxuron);

D. dinitrophenols and their derivatives (eg. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methysulphonyl-2,6-dinitro-N,N-dipropylaniline (nitralin);

F. phenylurea herbicides such as N'-(3,4-dichlorophenyl)-N,N-dimethylurea (diuron), N,N-dimethyl-N'-[3-(trifluoromethyl)phenyl]urea (flumeturon); N,N-dimethyl-N'-(4-isopropylphenyl)urea (isoproturon); and N'-(3-chloro-4-methylphenyl)-N,N-dimethyl urea (chlorotoluron).

G. phenylcarbamoyloxyphenylcarbamates such as 3-[methoxycarbonylamino]phenyl (3-methylphenyl)-carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil terbacil);

J. triazine herbicides such as 2-chloro-4-ethylamino-6-(i-propylamino)-1,3,5-triazine (atrazine), 2-chloro-4,6-di (ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron).

L. thiolcarbamate herbicides such as S-propyl dipropylthiocarbamate (vernolate); and S-ethyl di-isobutylthiocarbamate (butylate).

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl- -chloroacetyl-2',6'-diethylacetanilide (butachlor), the corresponding N-methoxy compound (alachlor), the corresponding N-i-propyl compound (propachlor) 3',4'-dichloro-propionanilide (propanil); and 2-chloro-(2-ethyl-6-methylphenyl)-N-(2-methoxy-1-methylethyl)acetamide.

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil).

Q. haloalkanoic herbicides such as 2,2-dichloropropionic acid (dalapon), trichloroacetic acid (TCA) and salts thereof, R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid, and 2-chloro-4-trifluoromethylphenyl 3-ethoxy-4-nitrophenyl ether.

S. miscellaneous herbicides including N,N-dimethyldiphenylacetamide (diphenamid), N-(1-naphthyl)-phthalamic acid (naptalam) and 3-amino-1,2,4-triazole.

T. bipyridylium herbicides such as those in which the active entity is the 1,1'-dimethyl-4,4'-bipyridylium ion (paraquat) and those in which the active entity is the 1,1'-ethylene-2,2'-bipyridylium ion (diquat).

U. Aryloxyphenoxypropionic acids and their derivatives (salts, esters, amides, and the like).

Examples of such acids are:
2-[4-(5-trifluoromethylpyridyl-2-oxy)phenoxy]propionic acid.
2-[4-(3-chloro-5-trifluoromethylpyridyl-2-oxy)phenoxy]propionic acid.
2-[4-(2,4-dichlorophenoxy)phenoxy]propionic acid.
2-[4-(5- or 6-chlorobenzoxazolyl-2-oxy)phenoxy]propionic acid
4-methyl-4-(4-trifluoromethylphenoxy)phenoxybut-2-enoic acid.

The invention is illustrated by the following examples in which all parts and percentages are by weight unless otherwise stated.

EXAMPLE 1

This example illustrates the preparation of 5-(2-chloro-6-fluoro-4-trifluoromethylphenoxy)-2-nitro-N- methylaminosulphonylbenzamide (compound 2 of Table 1).

(a) Preparation of 5-(2-chloro-6-fluoro-4-trifluoromethylphenoxy)-2-nitro-N-chlorosulphonylbenzamide.

To chlorosulphonyl isocyanate (20 ml) was slowly added 5-(2-chloro-6-fluoro-4-trifluoromethylphenoxy)-2-nitrobenzoic acid (18.98 g) with stirring. The mixture was heated slowly at 50° C. and stirred at this temperature for 1 hour during which time the mixture went clear and then formed a solid mass. The reaction mixture was cooled and cautiously diluted with hexane. The solid was filtered, washed with hexane and air dried. About 25 g of solid product was obtained whose structure was confirmed by infra red and nmr spectroscopy.

(b) 5-(2-chloro-6-fluoro-4-trifluoromethylphenoxy)-2-nitro-N-chlorosulphonylbenzamide (2.39 g) from stage (a) was dissolved in acetonitrile (20 ml) and cooled to about 6° C. in an ice bath. Aqueous methylamine (1.37 ml of 25% solution) was added dropwise with stirring, and the mixture was stirred at room temperature for 2 hours. The reaction mixture was concentrated to an oily residue which was dissolved in ethyl acetate and the solution washed with dilute hydrochloric acid, water and brine and dried over magnesium sulphate. The product was concentrated to a semi-solid and triturated with methylene chloride to give a pale yellow solid (0.76 g) having a melting point of 242° C. The structure (compound 2 of Table 1) was confirmed by elemental analysis, and infra red and nmr spectroscopy.

EXAMPLE 2

This Example illustrates the preparation of 5-(2-chloro-6-fluoro-4-trifluoromethylphenoxy)-2-nitro-N-(N-methoxy-N-methylamino)sulphonylbenzamide (compound 11 in Table 1).

5-(2-Chloro-6-fluoro-4-trifluoromethylphenoxy)-2-nitro-N-chlorosulphonylbenzamide (1 g) prepared as in Example 1 was dissolved in acetonitrile (5 ml) and pyridine (1 ml) was added dropwise. The solution was cooled to about 5° C. and a dry-ice/acetone condenser was fitted. The hydrochloric acid salt of dimethyl hydroxylamine (0.82 g) was added in portions and the mixture was stirred for 1½ hours. The mixture was concentrated and partitioned between ethyl acetate and water. The organic layer was washed with very dilute hydrochloric acid followed by brine and water and was dried over magnesium sulphate. The resultant solution was concentrated to give an oil which was triturated with ether-petrol (30–40), and an off-white solid was filtered off. The solid product was further purified by preparative thin layer chromatography (eluant-ether:hexane:acetic acid-60:40:5). The isolated product was recrystallised from ether/petrol to give a white solid (0.25 g) whose structure (compound 11 of Table 1) was confirmed by elemental analysis and nmr spectroscopy.

EXAMPLE 3

This example illustrates the preparation of 5-(2-chloro-6-fluoro-4-trifluoromethylphenoxy)-2-nitro-N-ethoxysulphonylbenzamide (compound 1 in Table 1).

5-(2-Chloro-6-fluoro-4-trifluoromethylphenoxy)-2-nitro-N-chlorosulphonylbenzamide (1 g) prepared as in Example 1 was dissolved in dry acetontrile (5 ml) and dry pyridine (1 ml) was added dropwise. The solution was stirred vigorously and absolute ethanol (1 ml) was added. The reaction mixture was stirred until the reaction was complete (¾ hour). The mixture was partitioned between ether and dilute hydrochloric acid solution, and the ether layer was dried over magnesium sulphate and evaporated under reduced pressure to give a buff solid. The solid was recrystallised from chloroform/hexane to give a white solid (0.43 g) having a melting point of 150° C. The structure (compound 1 of Table 1) was confirmed by elemental analysis and nmr spectroscopy.

EXAMPLE 4

This example illustrates the preparation of 5-(2-chloro-6-fluoro-4-trifluoromethylphenoxy)-2-nitro-N-dimethylaminosulphonylbenzamide (compound 5 in Table 1)

5-(2-Chloro-6-fluoro-4-trifluoromethylphenoxy)-2-nitro-N-chlorosulphonylbenzamide (2.39 g) prepared as in Example 1 was dissolved in dry acetonitrile (15 ml) and cooled to about 0° C. in an ice bath. A solution of dimethylamine (0.45 g) in dry acetonitrile was added dropwise, and the reaction mixture was allowed to warm to room temperature and stirred for ¾ hour. The mixture was allowed to stand overnight and was then concentrated to give an oily residue. Trituration with a small volume of ether gave a solid which was further purified with cold chloroform to give a product (1.11 g) having a melting point of 210° C. The structure (compound 5 in Table 1) was confirmed by elemental analysis and nmr spectroscopy.

EXAMPLE 5

This example illustrates the preparation of 5-(2-chloro-6-fluoro-4-trifluoromethylphenoxy)-2-nitro-N-(4-chlorophenyl)aminosulphonylbenzamide (compound 10 in Table 1).

5-(2-Chloro-6-fluoro-4-trifluoromethylphenoxy)-2-nitro-N-chlorosulphonylbenzamide, (2.39 g) prepared as in Example 1, was dissolved in dry acetontrile (20 ml) and cooled at 0° C. in an ice bath. A solution of 4-chloroaniline (1.28 g) in acetonitrile (10 ml) was added dropwise and the reaction mixture was stirred at room temperature for 2 hours during which time a precipitate formed. The reaction mixture was concentrated to a solid residue which was partitioned between ethyl acetate and very dilute hydrochloric acid. The extracted ethyl acetate layer was separated, washed and dried, and was then concentrated to give a solid. Trituration with chloroform gave a white solid, which was filtered and air dried. The product (1.55 g), whose structure (compound 10 of Table 1) was confirmed by elemental analysis and nmr spectroscopy, had a melting point of 225° C.

EXAMPLES TO 6 TO 10

This example illustrates the herbicidal properties of the compounds of Examples 1 to 5 respectively. The compounds were submitted to herbicide tests as described below.

The compound was formulated for test by mixing an appropriate amount of it with 5 ml of an emulsion prepared by diluting 160 ml of a solution containing 21.9 grams per liter of Span 80 and 78.2 grams per liter of Tween 20 in methylcyclohexane to 500 ml with water. Span 80 is a Trade Mark for a surface active agent comprising sorbitan monolaurate. Tween 20 is a Trade Mark for a surface active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed onto young pot plants (post-emergence test) of the species named in the Table below, at a rate equivalent to 1000 liters per hectare. Damage to plants was assessed 14 days after spraying by comparison with untreated plants, on a scale of 0 to 5 where 0 to 20% damage and 5 is complete kill. In the table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in Table II below.

$R^2$ is a group —OM where M is hydrogen or agriculturally acceptable cation, a group —$ZR^3$ where Z is oxygen or sulphur and $R^3$ is alkyl of 1-12 carbons, or a group —$NR^5R^6$ where $R^5$ and $R^6$ are each selected from the group consisting of hydrogen, alkyl of 1-12 carbons, alkoxy of 1-4 carbons, phenyl, a phenyl substituted with halogen, hydroxy, $C_1$ to $C_4$ alkyl, $C_1$ to $C_4$ alkoxy, $C_1$ to $C_4$ alkylthio, carboxy, $C_2$ to $C_5$ alkoxycarbonyl, cyano or phenyl.

2. A compound according to claim 1 wherein X is a halogen atom or a nitro group, $R^1$ is a hydrogen atom or a source of a hydrogen atom, and $R^2$ is a group —$OR^3$ wherein $R^3$ is an alkyl group containing from 1 to 12 carbon atoms.

3. A compound according to claim 1 wherein X is a halogen atom or a nitro group, $R^1$ is a hydrogen atom or a chlorine, bromine or iodine atom, and $R^2$ is a group —$NR^5R^6$ wherein $R^5$ and $R^6$ may each separately be

TABLE II

| Compound of Example | Rate of Application (kg/ha) | Pre or Post Emergence | Test Plants | | | | | | | | | | | | | | | | | | | | |
|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Ga | Xa | Ab | Co | Av | Dg | Al | St | Ec | Sh | Ag | Cn |
| 1 | 0.2 | Pre | 5 | 5 | 3 | 0 | 1 | 0 | 3 | 5 | 4 | 5 | 5 | 5 | 4 | 5 | 5 | 3 | 0 | 3 | 2 | 4 | 1 | 4 | 3 | 4 |
| | 0.1 | Post | 5 | 5 | 3 | 0 | 2 | 2 | 2 | 5 | 4 | 2 | — | 3 | 4 | 4 | 3 | 4 | 0 | 2 | 1 | 2 | 4 | 2 | 1 | 1 |
| 2 | 0.2 | Pre | 5 | 5 | 2 | 0 | 0 | 0 | 1 | 5 | 3 | 5 | 5 | 5 | 4 | 3 | 4 | 2 | 0 | 0 | 0 | 2 | 0 | 3 | 3 | 0 |
| | 0.5 | Post | 3 | 5 | 4 | 1 | 0 | 3 | 3 | 5 | 5 | 4 | — | 4 | 4 | 4 | 5 | 4 | 2 | 4 | 1 | 4 | 4 | 4 | 1 | 2 |
| 3 | 1.0 | Pre | 5 | 5 | 4 | 0 | 0 | 0 | 3 | 5 | 5 | 5 | 5 | 5 | 5 | 5 | 5 | 4 | 1 | 3 | 2 | 4 | 3 | 4 | 3 | 4 |
| | 0.5 | Post | 3 | 4 | 4 | 2 | 2 | 2 | 2 | 5 | 5 | 4 | — | 4 | 5 | 4 | 5 | 4 | 3 | 3 | 1 | 4 | 3 | 4 | 1 | 2 |
| 4 | 0.2 | Pre | 5 | 5 | 3 | 0 | 2 | 0 | 3 | 5 | 4 | 5 | 5 | 5 | 4 | 5 | 3 | 2 | 2 | 1 | 4 | 1 | 4 | 4 | 3 |  |
| | 0.5 | Post | 4 | 5 | 4 | 2 | 1 | 3 | 3 | 5 | 5 | 4 | — | 4 | 4 | 4 | 5 | 5 | 3 | 3 | 1 | 3 | 5 | 4 | 3 | 2 |
| 5 | 1.0 | Pre | 5 | 3 | 2 | 0 | 0 | 0 | 0 | 5 | 0 | 5 | 5 | 5 | 3 | 1 | 3 | 3 | 1 | 0 | 3 | 0 | 0 | 2 | 5 | 2 |
| | 0.1 | Post | 1 | 3 | 0 | 1 | 0 | 2 | 2 | 2 | 3 | 3 | — | 4 | 2 | 2 | 2 | 3 | 2 | 2 | 1 | 1 | 3 | 3 | 1 | 0 |

*Names of test plants in Table II*
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*

Ga *Galium aparine*
Xa *Xanthium spinosum*
Ab *Abutilon theophrasti*
Co *Cassia obtusifolia*
Ot/Av Oats (cultivated in pre-emergence test and *Avena fatua* (wild oats) in post-emergence test.
Dg *Digitaria sanguinalis*
St *Setaria viridis*
Ec *Echinocloa crus-galli*
Sh *Sorghum halepense*
Ag *Agropyron repens*
Cn *Cyperus rotundus*

I claim:

1. A diphenyl ether compound of the formula (I):

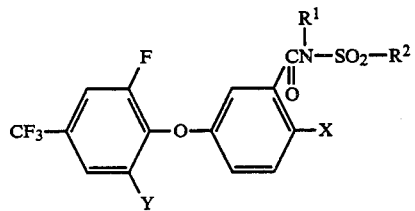

wherein
X is hydrogen, halogen, alkyl of 1 to 4 carbons, nitro or $CF_3$;
Y is fluorine or chlorine;
$R^1$ is hydrogen, chlorine, bromine or iodine, alkyl of 1 to 4 carbons, or an agriculturally acceptable cation; and hydrogen or an alkyl group containing from 1 to 12 carbon atoms, or one of $R^5$ and $R^6$ is an alkoxy group containing from 1 to 4 carbon atoms.

4. A compound according to claim 1 wherein X is a halogen atom or a nitro group, $R^1$ is a hydrogen atom or a chlorine, bromine or iodine atom, and $R^2$ is a group —$NR^5R^6$ wherein $R^5$ is hydrogen and $R^6$ is an unsubstituted phenyl group or a phenyl group substituted by halogen, hydroxy, ($C_1$ to $C_4$) alkoxy, ($C_1$ to $C_4$) alkylthio, carboxy, ($C_2$ to $C_5$) alkoxycarbonyl, cyano, optionally substituted phenyl or ($C_1$ to $C_4$) alkyl.

5. A process of inhibiting the growth of unwanted plants, which comprises applying to the plants, or to the locus thereof, a phytotoxic amount of a compound as claimed in claim 1.

6. Herbicidal compositions, comprising as an active ingredient a compound according to claim 1 in admixture with a carrier comprising a solid or liquid diluent.

* * * * *